United States Patent [19]
Dafni et al.

[11] Patent Number: 6,118,839
[45] Date of Patent: Sep. 12, 2000

[54] MULTIPLE SLICE CT SCANNER

[75] Inventors: Ehud Dafni, Ceasarea; David Ruimi, Natanya, both of Israel

[73] Assignee: Elscint Ltd., Haifa, Israel

[21] Appl. No.: 08/556,824

[22] Filed: Nov. 2, 1995

Related U.S. Application Data

[63] Continuation of application No. 07/915,549, Jul. 20, 1992, abandoned.

[30]     Foreign Application Priority Data

Jul. 24, 1991   [IL]   Israel ........................................ 098945

[51] Int. Cl.⁷ ...................................................... A61B 6/03
[52] U.S. Cl. ................................ 378/15; 378/19; 378/901
[58] Field of Search ................................ 378/4, 19, 15, 378/901

[56]             References Cited

U.S. PATENT DOCUMENTS

| | | | |
|---|---|---|---|
| 3,432,657 | 3/1969 | Slavin | 378/41 |
| 3,778,614 | 12/1973 | Hounsfield . | |
| 4,220,863 | 9/1980 | McBride et al. . | |
| 4,295,195 | 10/1981 | Hounsfield . | |
| 4,504,962 | 3/1985 | Moore | 378/19 |
| 4,630,202 | 12/1986 | Mori | 364/413.15 |
| 4,639,941 | 1/1987 | Hounsfield | 378/11 |
| 4,669,103 | 5/1987 | Barneu | 378/10 |
| 4,747,117 | 5/1988 | Albrecht et al. | 378/19 |
| 4,789,929 | 12/1988 | Nishimura et al. | 364/413.15 |
| 4,965,726 | 10/1990 | Heuscher et al. | 364/413.19 |
| 4,969,166 | 11/1990 | Hahn | 378/19 |
| 5,025,463 | 6/1991 | Saito et al. | 378/19 |
| 5,046,003 | 9/1991 | Crawford | 364/413.15 |
| 5,073,911 | 12/1991 | Ozahi et al. | 378/17 |
| 5,090,037 | 2/1992 | Toth et al. | 378/4 |
| 5,166,961 | 11/1992 | Brunnett et al. | 378/19 |
| 5,241,576 | 8/1993 | Lonn | 378/19 |
| 5,253,170 | 10/1993 | Kanamori et al. . | |
| 5,262,946 | 11/1993 | Herscher | 364/413.18 |
| 5,291,402 | 3/1994 | Pfoh | 364/413.14 |
| 5,323,439 | 6/1994 | Nobuta et al. | 378/19 |
| 5,341,460 | 8/1994 | Tam | 364/413.13 |
| 5,345,381 | 9/1994 | Wallschlaeger | 364/413.14 |
| 5,377,250 | 12/1994 | Hu | 378/15 |
| 5,448,609 | 9/1995 | Couch et al. | 378/19 |
| 5,960,056 | 9/1999 | Lai | 378/4 |

FOREIGN PATENT DOCUMENTS 52-75997   6/1977   Japan .

OTHER PUBLICATIONS

"Spiral CT Sanning for Fast and Continuous Volume Data Acquisition." by W. Kalender, P. Vock, and W. Seissler. pp. 55–64, Advances in CT, Springer–Verlag, Berlin, Heidelberg 1990.

"Computed Tomography Scanning with simultaneous Patient Translation" by C. Crawford and K. King. Medical Physics, vol. 17 No. 6 Nov./Dec. 1990 pp. 967–982.

*Primary Examiner*—David V. Bruce
*Attorney, Agent, or Firm*—Fenster & Company Patent Attorneys, Ltd.

[57]             ABSTRACT

A computerized tomography system wherein the X-ray source rotates about the subject and moves axially relative to the subject to provide a helical scan. A detector array includes a plurality of rows of detector elements extending axially and each element being of the same size to enable the acquisition of multiple planar data per rotation. The acquired data is reformatted into planar data by interpolating as a function of both the axial subject position and the axial detector element position.

37 Claims, 10 Drawing Sheets

MULTIPLE SLICE CT SCANNER

This application is a continuation of application No. 07/915,549, filed Jul. 20, 1992, now abandoned.

FIELD OF THE INVENTION

This invention is concerned with computerized tomographic (CT) systems and more particularly with systems equipped to simultaneously acquire multiple slice data in a single scan such as taught in the Application, Serial No. 090521 filed in Israel on Jun. 4, 1989.

BACKGROUND OF THE INVENTION

CT systems produce planar images along imaginary cuts through a subject. Each cut is referred to as a slice. Scanners comprise an X-ray source which revolves about an imaginary axis through a subject. The X-rays after passing through the subject impinge on an opposing array of detectors, which may also be revolving. Data for reconstruction of a single image includes a set of views corresponding to different projection angles, each view comprising radiation intensity data measured by detector elements.

A prior art CT study of a subject for obtaining successive planar images includes the following steps:

1. Putting the patient on the bed in a CT system gantry.
2. Scanning the patient. The scan includes the revolution of the X-ray source about the subject and acquisition of radiation intensity data per detector element per angle of revolution of the X-ray source.
3. Reconstructing the image. Optional display, archiving and/or filing.
4. Incrementing the bed to the position of the next slice.

Steps 2–4 are repeated as long as more slices are required. Step 3 may be concurrent with steps 2 and 4, but step 4 must be successive to step 2. Step 4 involves acceleration and de-acceleration of the bed as the bed must be stationary during the scan when successive planar images are acquired. Step 2 may involve acceleration and de-acceleration of the gantry to the proper rotational speed. Gantry acceleration and deceleration may, however, be circumvented by using a continuous rotation scanner such as provided, e.g., by slip-ring technology.

An ubiquitous problem encountered by CT systems is that heat builds up in the X-ray source as more scans are being performed. In prior art systems, when the scanning rate is such that heat build-up rate is higher than the cooling rate of the X-ray source and the X-ray source is at the limit of allowed stored heat, further scans must be delayed. The invention of the above listed Patent Application improves the utilization of the X-ray source; since that Application enables a CT scanner to simultaneously scan mutli-planar slices of the subject during single X-ray exposure and, therefore, unmanageable heat build-up is less likely to occur.

Other problems occur with the prior art CT scanners used to obtain a series of planar images. For example, the successive nature of the scanning process described hereinabove, prolongs the time during which the subject is imaged. The longer throughput time results in greater patient discomfort. The bed acceleration and de-acceleration add to the discomfort of the patient. Further, the patient is required to adjust his breathing cycle to the scanning rate so as to reduce motion related image artifacts. When the the examination period is longer, the breath control is more difficult resulting in more patient motion, both during scans and between scans. Patient motion, voluntary and involuntary, between scans decreases the repeatability that is desired between adjacent slices. In particular, oblique reformatting and 3-D images formed from series of planar images are adversely affected.

To overcome these problems, helical or spiral scanning systems are being investigated and developed. This type of scanning is described in the following references:

1. P. Slavin, U.S. Pat. No. 3,432,657 (1969).
2. I. Mori, U.S. Pat. No. 4,630,202 (1986).
3. H. Nishimura, U.S. Pat. No. 4,789,929 (1988).
4. W. A. Kalander, P. Vock and W. Seissler in Advances in CT (Springer-Verlag, Berlin, Heidelberg 1990, pp. 55–64).
5. C. R. Crawford and H. F. King, Med. Phys. 17(6), (1990) pp. 967–982 and references therein.

Essentially, with helical scanning scanners, the subject is continuously scanned while the gantry makes multiple rotations about the subject and the bed is moved relative to the gantry along the axis of rotation simultaneously with the rotation. Images of successive slices are reconstructed from sets of views using well known reconstruction algorithms.

In conventional non-helical; i.e., stationary bed CT scans made to image successive slices, the different views making up the different sets correspond to projections within the same plane. On the other hand, in the helical scans the different views making up the different sets correspond to projections in different planes. Therefore, non-modified conventional reconstruction yields artifacts; i.e., highly distorted images. To prevent such artifacts, the raw data is reformatted before backprojection into single plane data sets by interpolating between data measured at the same gantry angle but at different subject positions, providing data of different planes.

Hereinbelow, the theoretical slice sensitivity profile is defined as the response of the scanner to a small homogeneous object as a function of the object position along the axial direction. The slice width is defined as a full width at half maximum (FWHM) of the slice sensitivity profile.

In stationary-bed CT scans, the slice width is determined by collimators limiting the beam width or the length of the detector elements in the axial direction. In helical scans, data from different planes through the subject are mixed and the slice sensitivity profile is smeared. Therefore, the FWHM of the profile tends to be larger in a helical scan than in a stationary-bed scan for a given collimator setting. Also, the ratio between the full width at tenth maximum (FWTM) and the FWHM of the sensitivity profile, which is a measure of the quality of the slice width, is severly degraded.

Various schemes to improve the slice sensitivity profile in helical scans are discussed in the references cited hereinabove. These Include:

1. Linear and non-linear interpolation schemes;
2. Variable bed speeds associated with appropriate interpolation schemes; and
3. Reducing the bed speed so that the bed moves less than a whole slice width within a single gantry revolution.

None of these schemes, however, provides images of the quality obtained in prior art stationary bed CT systems for a given radiation dose applied to the subject. Furthermore, because of the increased time length of exposure required in helical scans, the available X-ray intensity is likely to be less than in stationary bed CT systems, thus further decreasing image quality.

In addition to the image quality problems exclusive to prior art helical scan CT systems, the prior art CT systems also encounter motion artifacts and partial volume artifacts.

To reduce motion artifacts it is advantageous in CT, In general, to have the scan time as short as possible. However, sometimes it is required to prolong the scan in order to reduce the statistical noise. There exists a technique whereby the gantry revolves multiple revolutions about the scanned subject and the data from the multiple revolutions are averaged before backprojection to yield an image of high statistics and reduced motion artifacts. The technique is disclosed by R. Hupke, in "Advances in CT" (Springer-Verlag, Berlin Heidelberg 1990, pp. 3–15).

Partial volume artifacts result from high spatial frequency variation of the radiation absorption coefficients in the subject. Such artifacts are reduced, in general, by using a smaller slice width. However, sometimes it is advantageous to use large slice widths so a large scanned volume may be covered by fewer slices. There exists a technique whereby data of several consecutive thin slices are averaged before backprojection to form one image. The technique is disclosed in the R. Hupke reference noted hereinabove.

The technique provides images with reduced partial volume artifacts and saves some of the reconstruction time, but it requires several scans to form one image and it is, therefore, inefficient.

BRIEF DESCRIPTION OF THE INVENTION

Accordingly, it is an object of the present invention to overcome the prior art problems general to CT scanning and specific to helical scanning.

It is a related object of the present invention to improve prior art helical scanning systems.

In accordance with one preferred embodiment of the present invention, a unique CT scanner system is provided, said system comprising:

a gantry, a bed for supporting a scanned subject, an X-ray source mounted on said gantry, means for rotating the X-ray source about the subject, an X-ray detector array on a side of the subject opposite to the X-ray source, said detector array comprising means for simultaneously detecting X-rays that have traversed multiple planar sections of said subject to acquire radiation density data, means for causing relative motion in an axial direction between the bed and the gantry while the X-ray source is revolving about the subject, and means for reconstructing images from said data where said reconstructing includes means for reformatting the acquired data into single plane data interpolating between data measured at different planar sections through said subject.

According to a feature of the invention, the means for reformatting comprises means for interpolating between data detected by the same and/or different detector elements in the same angular position during the revolution, but in different positions along the subject. The same angular position is understood herein to also include modular 180° and could, of course, include any "offset".

According to another feature of the invention, the detector array comprises multiple rows of detectors, the row extending in a direction parallel to the axis of rotation of the gantry; i.e., in the axial direction.

According to yet another feature of the invention, the multiple detectors are used either to acquire multiple slice data simultaneously per revolution to acquire wider slices per revolution.

BRIEF DESCRIPTION OF THE DRAWINGS

The above mentioned and other objects and features of the present invention will be best understood when considered in the light of the following description made with reference to the accompanying drawings wherein;

FIG. 5 shows the helical scanner of the present invention with multiple detectors extending in the Z direction, FIG. 6a graphically and pictorally illustrates the data acquired in a prior art helical scanner as the gantry rotates and the subject translates/revolution, FIG. 6b graphically and pictorally illustrates the data acquired in the inventive helical scanner as the gantry rotates and the subject translates/revolution, FIG. 7 graphically shows effective slice width per nominal slice width versus subject translation motion speed for different quantities of rows.

GENERAL

Figure 1:
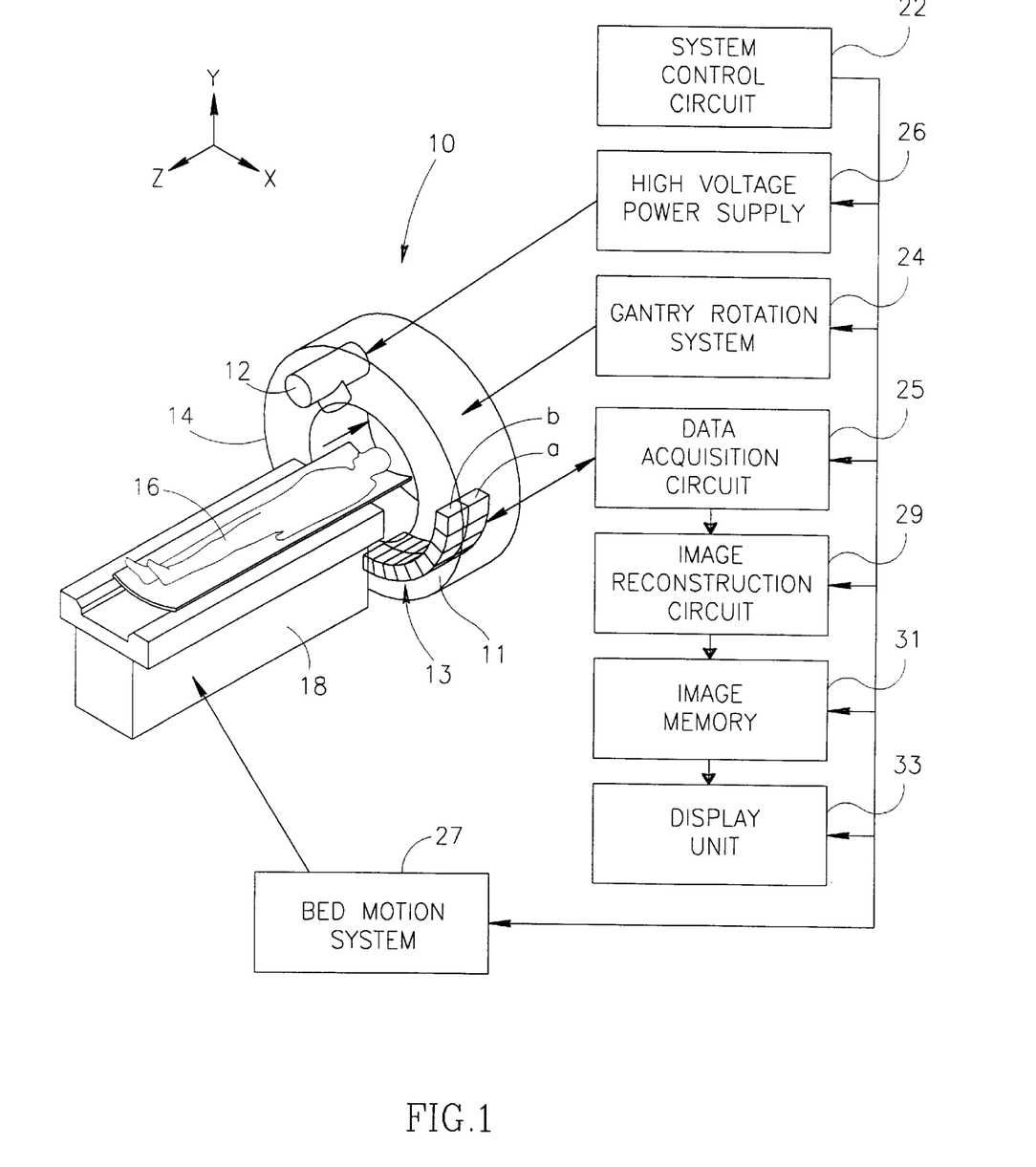
FIG. 1 is a pictorial-block diagram of a scanner according to the present invention, FIG. 2 pictorially illustrates detectors extending in the axial or Z direction enabling the acquisition of multiple slice data during a single rotation.

FIG. 1 is a general layout of a third generation (rotate—rotate) scanner 10 comprising an X-ray source 12 mounted onto a gantry 14. A subject 16 to be scanned is supported by means of a bed 18. Fan-shaped X-rays which traverse a planar section through the subject 16 are detected by detector array 13.

A cartesian coordinate system 15 is defined in FIG. 1. Therein the Z axis is along an imaginary longitudinal axis that is the rotational axis of the gantry. It may be coincidental to the longitudinal axis through the subject. The Y axis is along a straight line from X-ray source 12 to the center of revolution of gantry 14. The X axis is perpendicular to each of the above axes.

As gantry 14 revolves about the Z axis, so does the coordinate system 15 relative to a stationary surrounding.

According to preferred embodiments of the present invention detector array 13 comprises multiple detector elements such as detector elements 11a and 11b arranged in multiple rows. For illustration, two rows are shown in FIG. 1 and denoted by letters a and b. However, the number of rows may be larger than two. Detector elements 11 of each row detect the X-rays that have passed through multiple planar sections in subject 16. The apparatus illustrated in FIG. 1 is referred to as multiple slice CT scanner.

Figure 2:
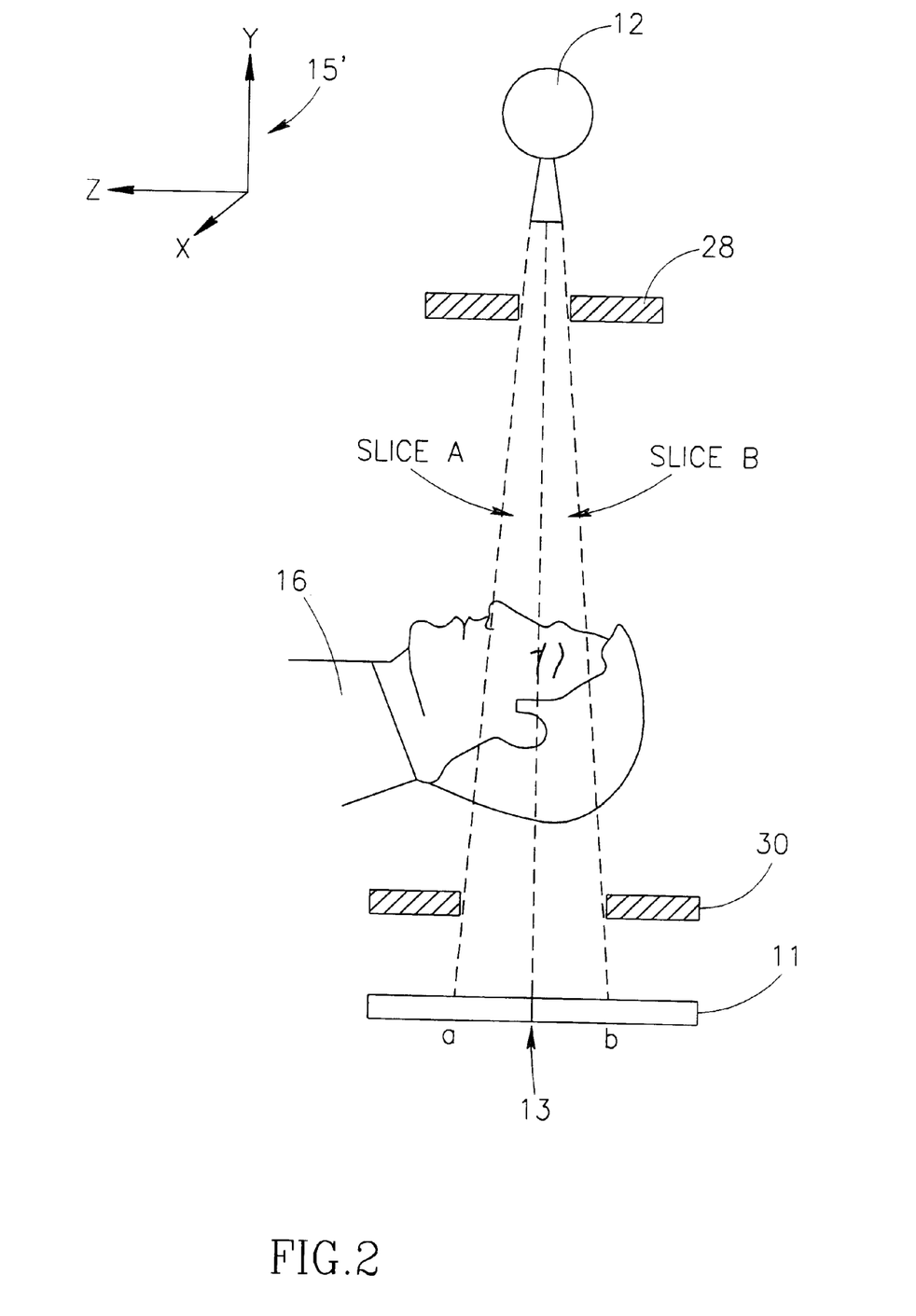

FIG. 2 is a schematic view of one preferred embodiment of the apparatus shown in FIG. 1. In this embodiment, there are two rows of detector elements 11 in detector array 13. Also in this embodiment, the X-ray source 12 has a single focal spot along the Z axis shown in the coordinate system 15'. Two planar sections of subject 16, slice A and slice B, are simultaneously scanned. X-rays from X-ray source 12 are collimated by collimators 28 and 30 so that they traverse subject 16 through the adjacent planar sections denoted as slice A and slice B and are detected by detector array member elements 11 in rows denoted by letters a and b, respectively.

Figure 3:
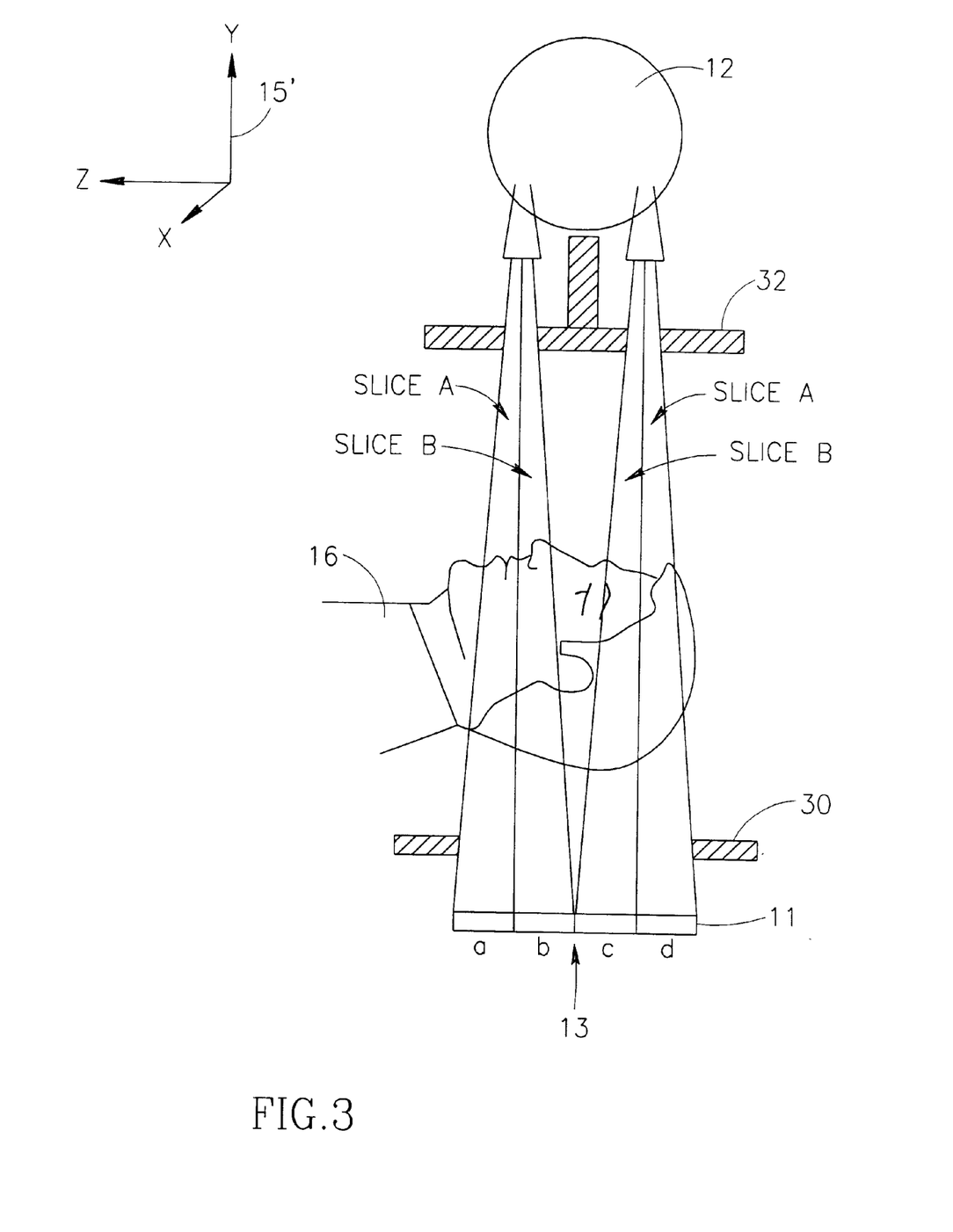
FIG. 3 illustrates the use of multiple focal points and multiple detectors extending in the Z direction to further increase the slice data acquired per rotation, FIG. 4 indicates a prior art helical scanner.

FIG. 3 is a schematic view of another preferred embodiment of the apparatus shown in FIG. 1. In this embodiment of the present invention there are n rows of detector elements in detector array 13, n being an integer equal to or larger than 2. The X-ray source in FIG. 3 uses multiple focal spots displaced from each other along the Z axis. In the embodiment of FIG. 3, n planar sections of subject 16 are simultaneously scanned during a single rotation.

Explicit values shown for FIG. 3 are n=4 and two focal spots. X-rays from X-ray source 12 are collimated by collimator sets 32 and 30 so that they traverse subject 16 through four planar sections denoted as slices A, B, C and D and detected by detector array member elements 11 in rows denoted by letters a, b, c, and d, respectively.

Returning now to FIG. 1, the various operations of the computerized tomography system are controlled by means such as system control circuit 22. Thus, circuit 22 controls, among other things, the operation of the rotation system 24 of the gantry 14. More particularly, gantry 14 with X-ray source 12 revolve about the Z axis powered and controlled by gantry rotation system 24 while X-ray source 12 is energized by high voltage power supply 26. Subject 16 is positioned within aperture of gantry 14 by means of bed motion control system 27.

The intensity of the radiation after its traversal of the subject 16 is detected by detector array 13 and acquired by data acquisition circuit 25. Radiation intensity data from rays traversing subject 16 over a range of at least 180° in the gantry revolution plane are used to reconstruct an image by means of image reconstruction circuit 29 and image memory 31. Display unit 33 is used to display the reconstructed image.

According to a preferred embodiment of the present invention subject 16 may be moved by means of bed 18 under the control of bed motion system 27 simultaneously with gantry rotation, such that the Z position of subject 16 is synchronized with angle of rotation of gantry 14. The direction of the motion of subject 16 may be along the Z axis or at oblique angles to the gantry 14 revolution plane; i.e., the X-Y plane. Furthermore, in this embodiment of the present invention, the rotating portions of gantry 14 may revolve continuously for multiples of complete revolutions such as is possible with slip ring construction. The apparatus described hereinabove is particularly useful for performing helical scans.

Figure 4:
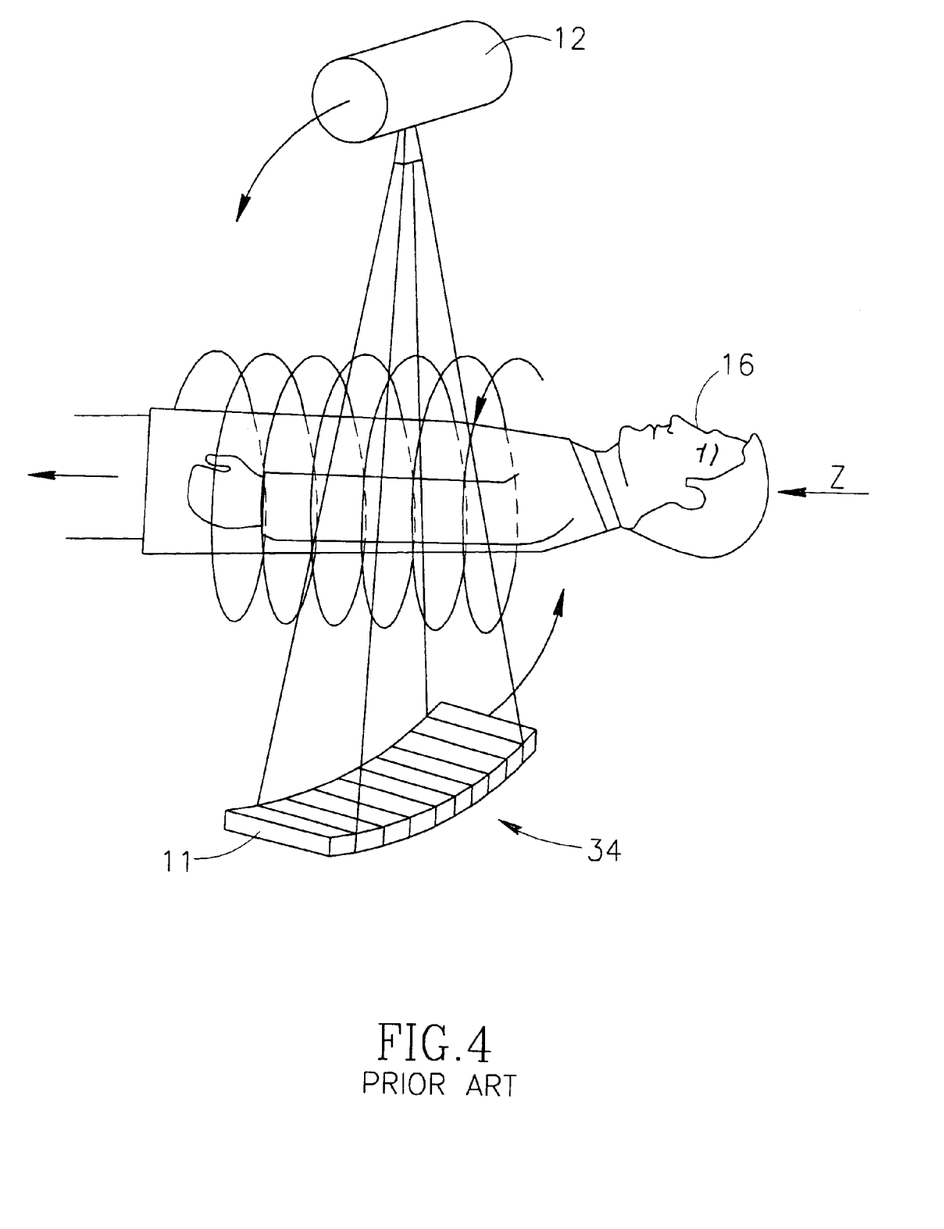

FIG. 4 illustrates the helical scans of prior art CT systems. Subject 16 moves along the Z axis while X-ray source 12 revolves about the subject. Fan shaped X-ray beams are detected by detector array 34 comprising a single row of detector elements 11. The X-ray beam in effect describes a helix in its path about subject 16.

The FWHM of the slice sensitivity profile for a stationary-bed scan under given conditions is denoted hereinbelow as the nominal slice width. The FWHM of the slice sensitivity profile of the helical scan is denoted hereinbelow as the effective slice width. It is desirable to have the effective slice width be as nearly equal to the nominal slice width as possible. However, helical scans tend to have an effective slice width larger than the nominal slice width. The effective slice width becomes smaller as the relative movement of the subject 16 decreases. On the other hand, it is desirable for the relative movement of the subject 16 to be as large as feasible so as to scan a large volume in a short time.

Figure 5:
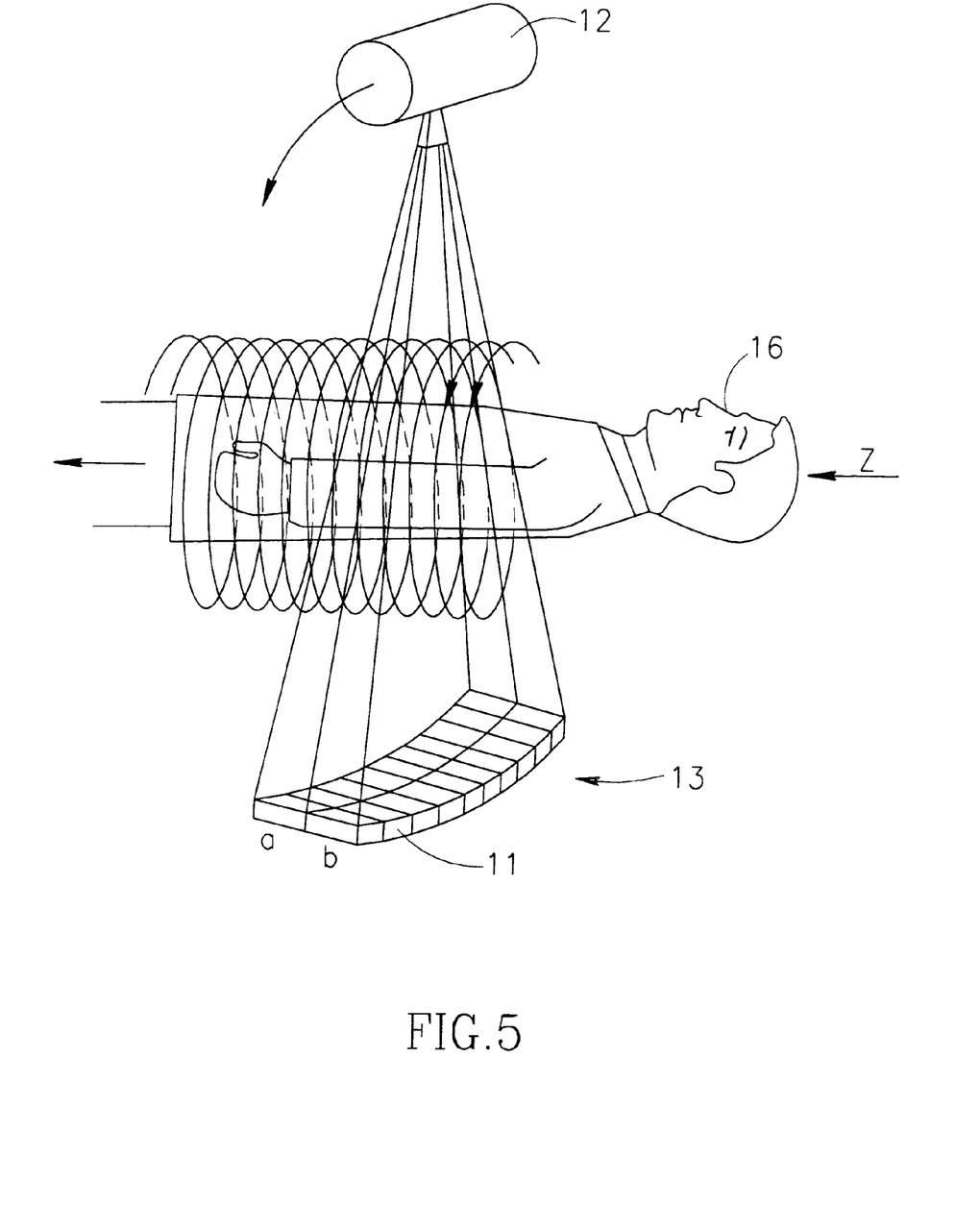

FIG. 5 illustrates helical scans performed on the multiple slice CT scanner described hereinabove according to the present invention. For simplicity, FIG. 5 illustrates the case of two rows of detector elements 11 extending in the Z direction. In FIG. 5 the fan beam impinging on the row denoted by letter "a" forms an imaginary or effective helix "c" about the subject 16 while the fan beam impinging on the row denoted by letter "b" forms an imaginary helix "d" about the subject 16. Helix c and helix d are interleaved. It is apparent from FIG. 5 that in the general case of n rows of equally sized detector elements 11 in detector array 13 there are n interleaved helices.

According to one preferred embodiment of a system using the apparatus described hereinabove, the nominal slice width is considered the slice width obtained in a stationary-bed scan using each row of equally sized detector elements 11 for a single slice. This is the mode wherein multiple slices are acquired in a single scan. Helical scan image reconstruction involves interpolation of measurements made by detector elements 11 in two different rows at different relative subject positions.

Figure 6A:
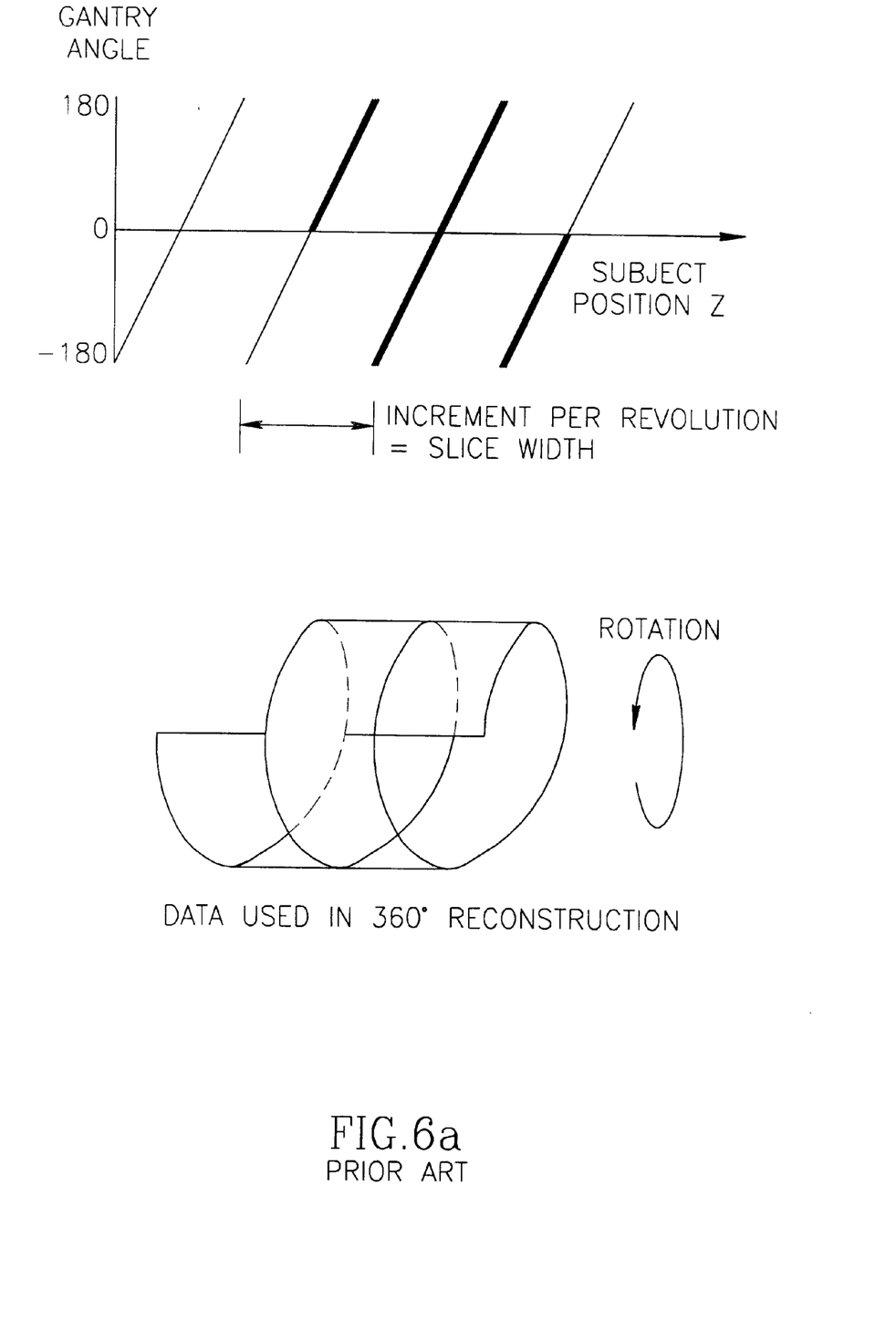
Figure 6B:
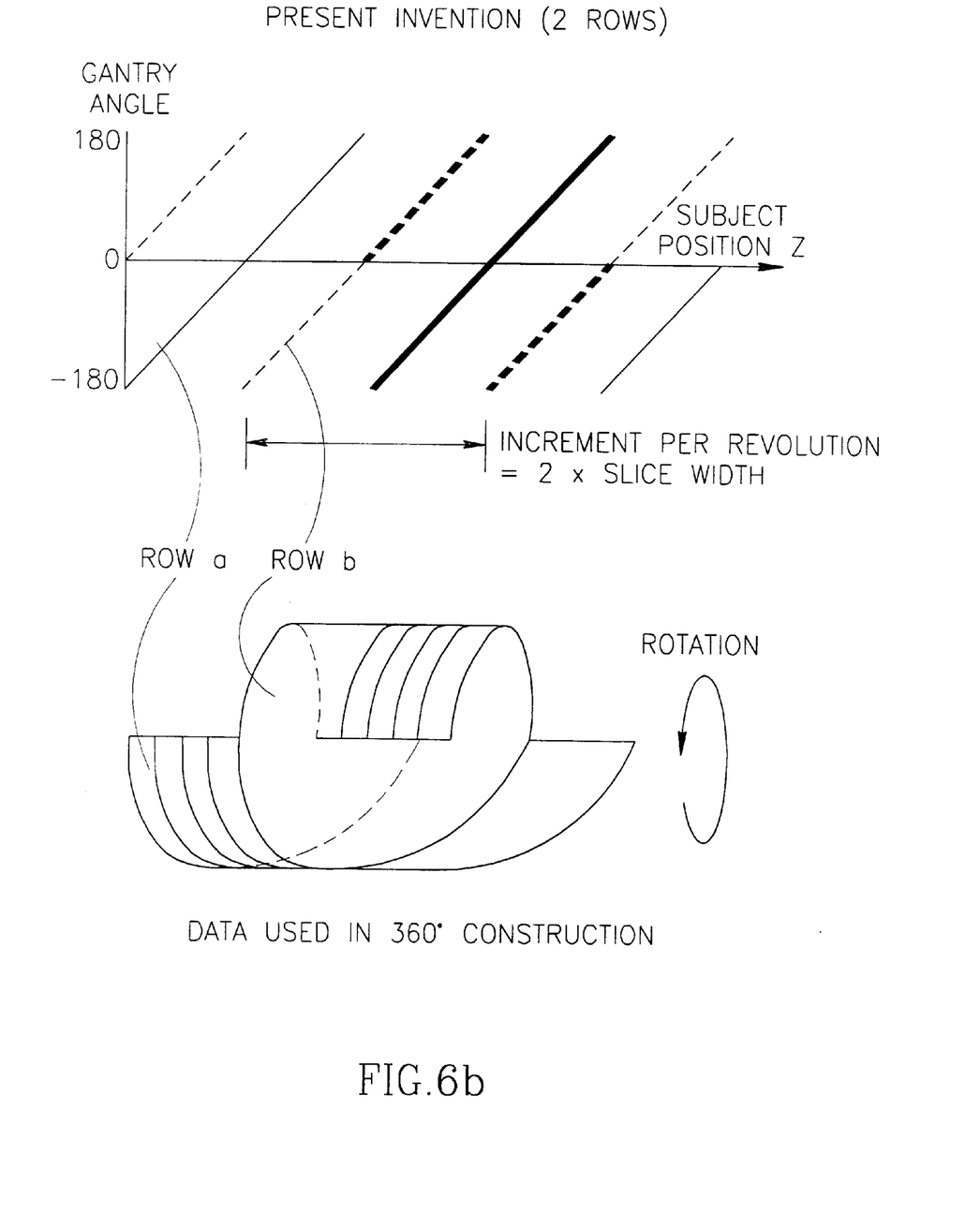

FIGS. 6a and 6b graphically illustrate the gantry angle versus subject position in the prior art and in the system of FIG. 5 when used in the mode described immediately hereinabove, and more particularly, illustrates certain advantages of the multiple slice helical scan system. The number of rows n of detector elements 11 in detector array 13 is exemplarily shown as n=2 for FIG. 6b. Effectively, data of identical quality may be acquired by the systems of FIGS. 4 and 5 where the speed of the subject motion in FIG. 6b is twice as great as in FIG. 6a. Thus, with a multiple slice system it is possible to scan a longer section of the subjet in a given time. Alternatively, if the two systems are used at the same subject speeds, a multiple amount of data of subject 16 is acquired using the system of FIG. 5 as compared to the amount of data acquired with the prior art (FIG. 4). Thus, the system of FIG. 5 with the same subject speed as in the system of FIG. 4 yields images of a higher quality.

In the FIGS. 6a and 6b, the segments of the helical scan in which useful data is obtained to reconstruct 360° images are schematically shown with heavy lines and pictorally shown as segments of helices. It is apparent that with the system of FIG. 5 approximately twice as much useful data is acquired as compared with the data acquired with the system of FIG. 4.

As illustrated in FIG. 6a for 360° reconstruction, data from the detector element in its previous 0 to 180 degree location and in its succeeding −180 to 0 degree location are interpolated (weighted interpolation) with the data of the slice being imaged to reformat the data into single plane data. FIG. 6b illustrates that with the multi-slice helical scan more data is acquired. The data acquired includes data from the detector element used for acquiring slice B in its previous 0 to 180 degree position and in its succeeding −180 to 0 degree position interpolated (weighted interpolation) with the data of the detector element imaging slice A.

Figure 7:
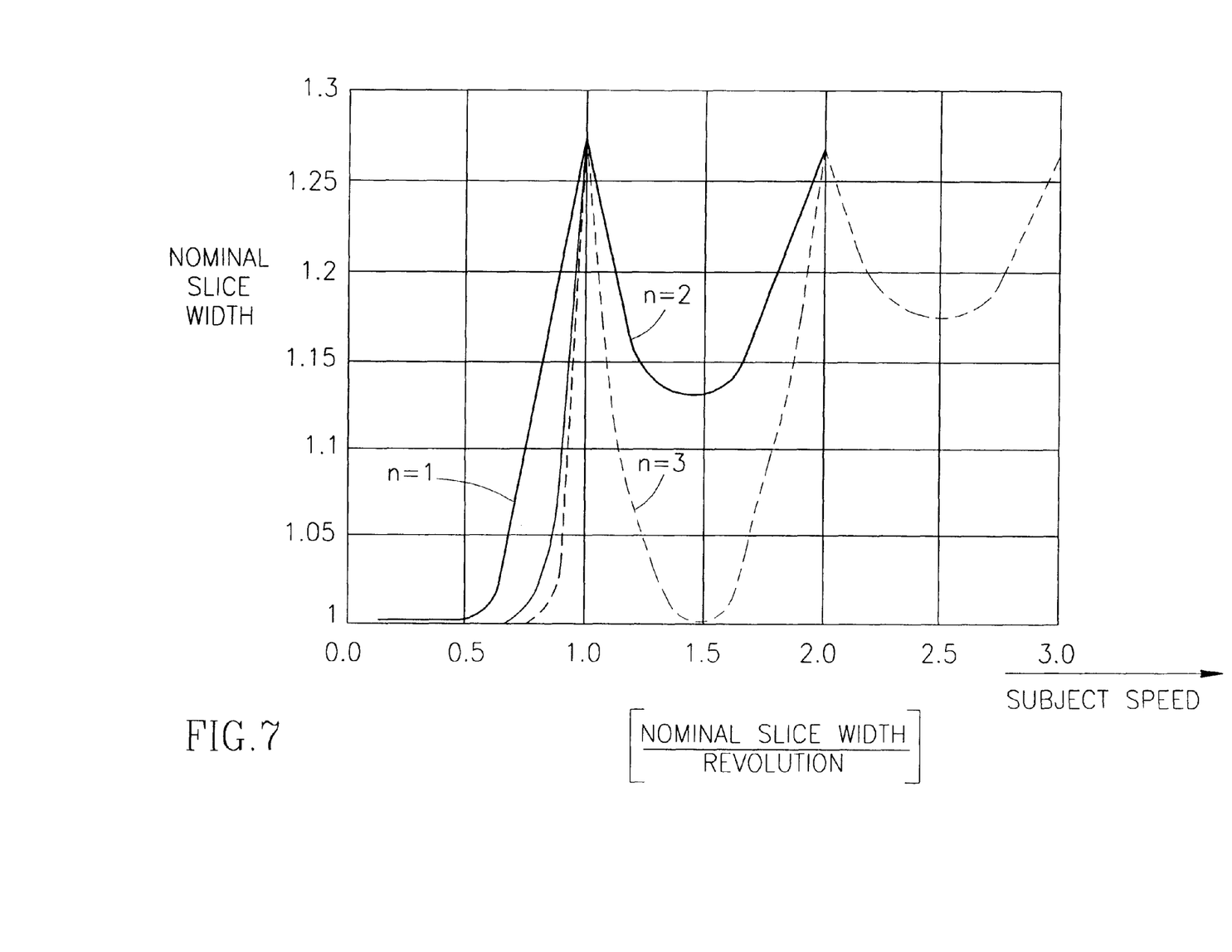

FIG. 7 illustrates the ratio of the effective slice width to nominal slice width as a function of the velocity of the subject 16 for the case of linear interpolation. The heavy solid line graph represents the prior art helical systems such as shown in FIG. 4. The light solid line graph represents dual slice inventive system such as illustrated in FIG. 5 and the dashed line graph represents a triple slice helical system.

FIG. 7 indicates that on a multiple slice CT scanner a higher subject 16 velocity is possible than on a single slice CT scanner with the same or even an improved slice sensitivity profile. Therefore, with multiple slice CT scanning a given volume of subject 16 may be scanned in a shorter time. In particular, on an "n" slice CT scanner with a velocity for subject 16 of n nominal slice widths per revolution of X-ray source 12, the effective slice width is the same as obtained for a single slice CT scanner at a subject 16 velocity of one nominal slice width per revolution of X-ray source 12.

According to another preferred embodiment of a system using the multiple slice CT scanner described hereinabove, the nominal slice width is considered the slice width obtained in a stationary-bed scan using data of multiple rows of detector elements 11 added together for a single combined slice. Image reconstruction involves interpolation of data measured simultaneously by the detector elements of m adjacent rows and the data measured simultaneously or at a different time by another detector element of one of the m rows or an adjacent row; where m is an integer larger than 1 and smaller or equal to n; where n is the number of rows of detector elements 11 in detector array 13.

Figure 8:
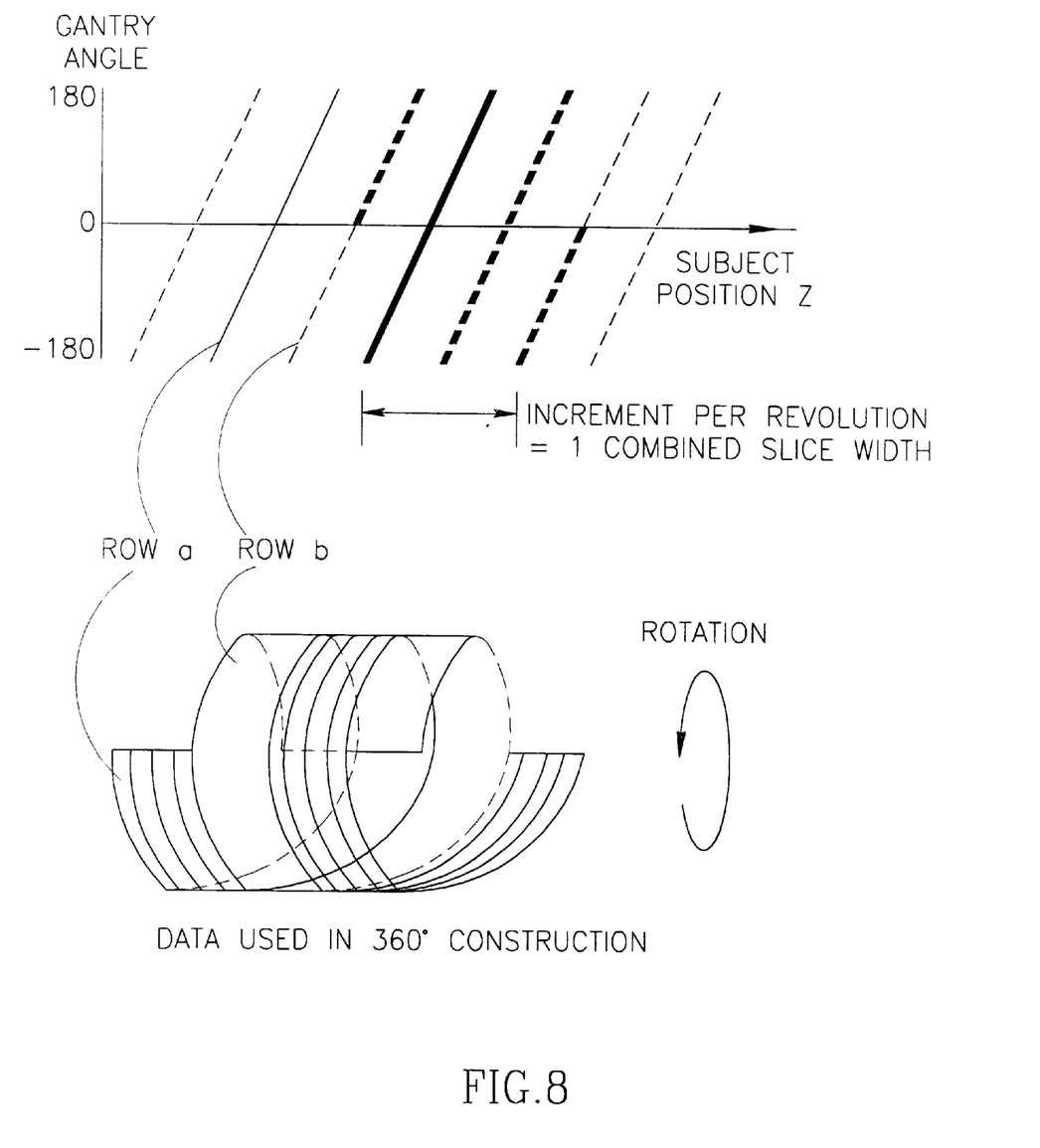
FIG. 8 graphically and pictorally illustrates the data acquired in the inventive helical scanner when multiple slices acquired per revolution are combined into one slice, and FIG. 9 graphically shows slice sensitivity profiles as a function of position along the Z axis for different quantities of rows of detector elements.

For example, FIG. 8 graphically illustrates the gantry angle versus subject 16 position in the system of FIG. 5 used as described herein. The number of rows of equally sized detector elements 11 in detector array 13 and the number of adjacent rows used in reconstruction are explicity set to n=m=2. Thus, the data of two rows of detector elements are used as the data for a combined slice. In FIG. 8 the segments of the helical scans from which useful data to reconstruct a 360° image obtained are schematically shown by darkened lines and pictorally illustrated by sections of helices. Thus, FIG. 8 shows that both slices A and B are acquired. Data from the detector element imaging slice B in its previous 0 to 180 degree location and data from the detector element acquiring slices A in its succeeding −180 to 0 degree location are interpolated with the data from the detector element acquiring slices A and B. Then the data is used to provide a single image.

Figure 9:
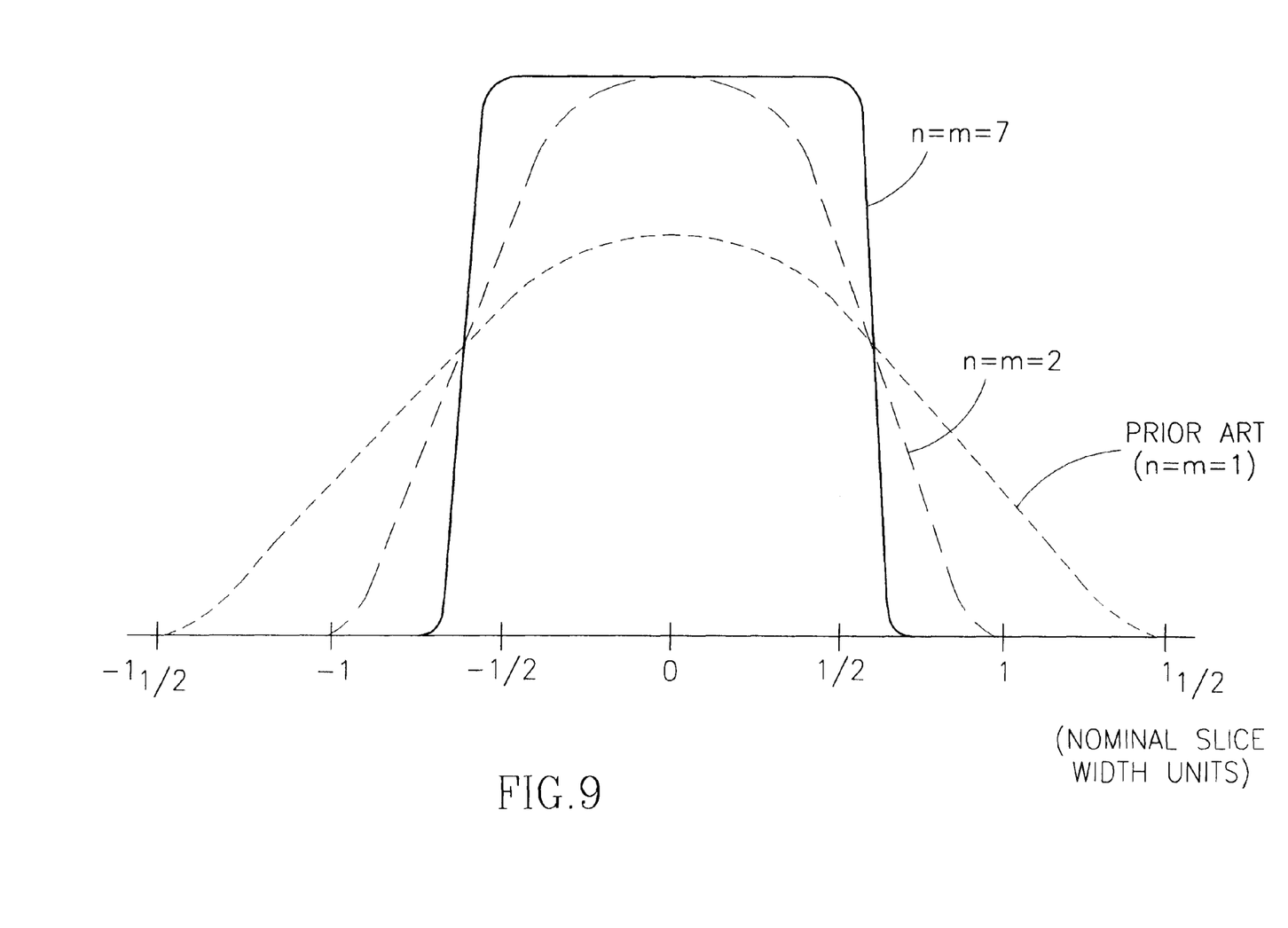

FIG. 9 shows different slice sensitivity profiles each obtained according to the scheme of FIG. 8 with a different number n of rows of detectors. The effective slice width discussed hereinabove is the FWHM of the curves in FIG. 9. For simplicity, a linear interpolation scheme between measurements at the same gantry angle and a subject velocity of one nominal slice width per revolution of X-ray source 12 is assumed. FIG. 9 shows graphically that the slice sensitivity profile becomes narrower as the number of rows n of detector elements increase.

FIGS. 5–9 illustrate, for reasons of simplicity, a linear interpolation scheme between measurements at the same gantry angle and constant bed speed. Those familiar with the art of computerized tomography will appreciate that there is an advantage in using the embodiments described hereinabove over prior art for almost any interpolation scheme and/or bed velocity scheme.

Returning again to FIG. 1, according to the present invention, another preferred embodiment using the multiple slice CT scanner described hereinabove includes the capability of continuous multiple revolutions of the multi-slice CT scanner about subject 16 but does not require simultaneous motion of subject 16. According to this embodiment, intensity data for X-rays from X-ray source 12 which have traversed multiple planar sections through subject 16 are measured simultaneously during multiple consecutive revolutions of gantry 14 while bed 18 is stationary. Data measured at the same gantry angle by the same detector element 11 are averaged and used in reconstruction to yield multiple images which have the statistics level of a long exposure, but are generally free from motion related artifacts.

The advantage of this embodiment over the prior art is that multiple planar sections of subject 16 are simultaneously scanned to obtain multiple images. Thus, simultaneous scanning reduces the time of the study thereby cancelling the increased time and compensating for the increased X-ray source 12 load associated with multiple revolution scans.

Alternatively, in yet another preferred embodiment of the present invention, the data from adjacent planar sections of the multiple planar sections measured simultaneously during one revolution of the gantry are averaged and single images are reconstructed corresponding to planar sections having substantially the combined width of the individual multiple planar sections which are generally free from partial volume artifacts.

Finally, the two preferred embodiments described immediately hereinabove may be combined to form a CT scanner system wherein single images which are generally free from motion and partial volume artifacts are reconstructed from averaged multiple planar section data acquired in multiple gantry revolutions.

Persons skilled in the art of X-ray detection will appreciate that the present invention is not limited to a particular detector array, but rather to any apparatus that yields the intensity and position of the X-rays. In particular, detector array 13 may comprise multiple detector elements, multiple segmented detector elements, an array of single detectors or a continuous media responsive to X-rays that also provides position readouts.

Although the invention has been described with reference to particular embodiments the invention is not confined to the specific embodiments described hereinabove but rather to the general scope of the claims.

What is claimed is:

1. A computerized tomography (CT) scanner system comprising:

a gantry, a bed for supporting a scanned subject within an aperture in said gantry, an X-ray source mounted on said gantry, means for revolving said X-ray source about said subject, an X-ray detector array on a side of said subject opposite from said X-ray source, said detector array comprising multiple rows of axially extending detectors for simultaneously detecting X-rays that have traversed multiple planar sections of said subject to thereby acquire radiation intensity data, means for causing relative motion in an axial direction between said gantry and said subject during the scans so that said data are acquired by said detector array while said X-ray source revolves about said subject during the relative motion along said axial direction to provide a helical scan with continuously different bed positions relative to said source and to said detector array, means for reconstructing images from said data including means for reformatting said data into single plane data, and wherein said means for reformatting comprises means for interpolating between data acquired by a detector element of one row at a given bed position and gantry angle, and data acquired by another detector element in a following row and adjacent to the detector of the first row at the given bed position and gantry angle or at different bed positions and gantry angles and differing by an integer multiple of $\pi$.

2. The computerized tomography system of claim 1 wherein said detectors in the multiple rows are of the same size.

3. The computerized tomography system according to claim 1 where said interpolation between data is linear as a function of said bed positions.

4. The computerized tomography system according to claim 1 where said interpolation between data is non-linear as a function of said bed positions.

5. The computerized tomography system according to claim 1 where said detector array revolves about said subject along with said X-ray source.

6. The computerized tomography system according to claim 1 where said detector array is stationary.

7. The computerized tomography system according to claim 1 where said detector array nutates.

8. The computerized tomography system according to claim 1 where said detector array comprises multiple single detector elements.

9. The computerized tomography system according to claim 1 where said detector array comprises segmented detector elements.

10. The computerized tomography system according to claim 1 where said X-ray source has a single focal spot.

11. The computerized tomography system according to claim 1 where said X-ray source has multiple focal spots.

12. The computerized tomography system of claim 1 where said means for reconstruction of images corresponding to single planar sections, enable a bed speed such that more than a planar section width is acquired by said detectors per one revolution of said X-ray source.

13. A computerized tomography (CT) scanner system comprising:

a gantry, a bed for supporting a scanned subject within an aperture in said gantry, an X-ray source mounted on said gantry, means for revolving said X-ray source about said subject, an X-ray detector array on the side of said subject opposite from said X-ray source, said detector array comprising multiple rows of axially extending detectors for simultaneously detecting X-rays that have traversed multiple planar sections of said subject to thereby acquire radiation intensity data, means for causing relative motion in an axial direction between said gantry and said subject during the scan so that said data are acquired by said detector array while said X-ray source revolves about said subject during the relative motion along said axial direction to provide a helical scan with continuously different bed positions relative to said source and to said detector array, means for reconstructing images from said data including means for reformatting said data into single plane data where said single plane data is obtained by interpolating at least part of said intensity data, said means for reformatting comprising means for interpolating between intensity data acquired simultaneously at a given bed position by detector elements each in one of multiple rows and at a given gantry angle, and intensity data acquired by a detector element in an axially adjacent one of said multiple rows at the given gantry angle or at a gantry angle differing by an integer multiple of $\pi$.

14. A computerized tomography (CT) scanner system comprising:

a gantry, a bed for supporting a scanned subject within an aperture in said gantry, an X-ray source mounted on said gantry, means for revolving said X-ray source about said subject, an X-ray detector array on the side of said subject opposite from said X-ray source, said detector array comprising multiple rows of axially extending detectors for simultaneously detecting X-rays that have traversed multiple planar sections of said subject to thereby acquire radiation intensity data, means for causing relative motion in an axial direction between said gantry and said subject during the scan so that said data are acquired by said detector array while said X-ray source revolves about said subject during the relative motion along said axial direction to provide a helical scan with continuously different bed positions relative to said source and to said detector array, means for reconstructing images from said data including means for reformatting said data into single plane data, where said data are obtained by interpolating at least part of the data as a function of both the bed position and the position of the detectors, said data being acquired by adjacent detectors at the same gantry angle, and means for interpolating between data acquired from multiple planar sections of the subject, said data being acquired simultaneously by detectors in adjacent rows.

15. A computerized tomography (CT) scanner system comprising:

a gantry, a bed for supporting the scanned subject within an aperture in said gantry, an X-ray source mounted on said gantry, means for revolving said X-ray source about said subject, an X-ray detector array on a side of said subject opposite from X-ray source, said detector array comprising multiple rows of axially extending detectors for simultaneously detecting X-rays that have traversed multiple planar sections of said subject to thereby acquire radiation intensity data, means for causing relative motion in an axial direction between said gantry and said subject during the scan so that said data is acquired by said detector array while said X-ray source revolves about said subject during the relative motion along said axial direction to provide a helical scan with continuously different bed positions relative to said source and to said detector array, and means for reconstruction of images from said data where said reconstruction includes means for reformatting said data into single plane data, where said data is obtained by interpolating at least part of the data as a function of both the bed position and the axial position of the detectors, said data being acquired by adjacent detectors at the same gantry angle or at gantry angles differing by an integer multiple of $\pi$.

16. The computerized tomography system according to claim 15 where the seed of the relative motion in the axial direction is substantially constant.

17. The computerized tomography system according to claim 15 where the speed of the relative motion in the axial direction is variable while said X-ray source revolves at a constant speed.

18. A computerized tomographic system including:

a gantry, a bed for supporting a scanned subject in an aperture of said gantry where said bed is stationary during the scan but movable between scans, an X-ray source on said gantry, means for rotating said X-ray source at a substantially constant speed about said subject for two continuous revolutions, an X-ray detector array mounted on the side of said subject opposite said X-ray source, means for revolving said detector array about said subject simultaneously with the rotation of said X-ray source, said detector array comprising multiple detector elements axially extending for simultaneously detecting X-rays that have traversed multiple planar section in said subject, means for averaging data detected at the same gantry angle during consecutive revolutions of said X-ray source, and means for reconstructing multiple images corresponding to the planar sections measured simultaneously by said detector array, said image being reconstructed from averaged data of multiple revolutions of the X-ray source about the same multiple planar sections in said subject.

19. A method of computerized tomography including the steps of:

supporting a scanned subject within an aperture of a gantry, mounting an X-ray source on said gantry, revolving said X-ray source in a substantially constant speed about said subject for at least two continuous revolutions, mounting an X-ray detector array on the side of said subject opposite to said X-ray source, said detector array comprised of a plurality of detector elements extending axially and being of substantially the same size, simultaneously detecting X-rays that have traversed multiple planar sections in said subject, averaging data obtained from X-rays received from adjacent planar sections detected at the same gantry angles during consecutive revolutions of said X-ray source, said data being unweighted with regard to the size of the elements, and reconstructing single images corresponding to planar sections with widths substantially the sum of the widths of the adjacent ones of the multiple planar sections and averaged over multiple rotations of said gantry.

20. A computerized tomography system including:

a gantry, a bed for supporting a scanned subject in an aperture of said gantry, said bed being stationary during a scan but movable between scans, means for mounting an X-ray source on said gantry, an X-ray detector array comprising multiple detector elements extending axially, said multiple detector elements being mounted on said gantry on the side of said subject opposite to said X-ray source for simultaneously detecting X-rays that have traversed multiple planar sections in said subject, means for rotating said gantry about said subject at least twice consecutively in the same axial position to acquire at least two sets of data from each of said adjacent multiple planar sections, means for averaging the acquired at least two sets of data received from each of the adjacent multiple planar sections detected at the same gantry angle during the at least two consecutive revolutions of said X-ray source while said bed is stationary, and means for reconstructing single images from the averaged data, said reconstructed single images being of planar sections of the scanned subject with widths that are substantially the sum of the widths of at least two of the adjacent ones of the multiple planar sections.

21. A method of computerized tomographic (CT) scanning of a subject comprising the steps of:

mounting an X-ray source on a gantry, supporting the subject on a bed within an aperture in said gantry, revolving said X-ray source about said subject, simultaneously detecting X-rays that have traversed multiple planar sections of said subject to thereby acquire radiation intensity data, said step of simultaneously detecting comprising using a detector array comprising multiple rows of axially extending detector elements, causing relative motion in an axial direction between said gantry and said subject during the scan so that said data is acquired by said detector array while said X-ray source revolves about said subject and during the relative motion along said axial direction to provide a helical scan with said subject continuously moving to different axial positions during said scan, reconstructing images from said data where said reconstruction includes reformatting into single plane data, and said reformatting comprising interpolating said data based on the positions of said subject and the axial positions of the detecting detector elements during said scan.

22. The method of computerized tomography of claim 21 wherein said step of simultaneously detecting comprises using multiple rows of detectors each detector being of the same size and extending in a direction parallel to said axial direction.

23. The method of computerized tomography according to claim 21 where the relative motion speed is variable.

24. The method of computerized tomography of claim 21 wherein said interpolating step comprises interpolating data acquired simultaneously by adjacent detector elements each in one of multiple rows at a given gantry angle with data acquired by a detector element in one of said multiple rows at the given gantry angle or another gantry angle differing by an integer multiple of $\pi$.

25. The method of computerized tomography according to claim 21 including the step of revolving said detector array about said subject along with said X-ray source.

26. The method of computerized tomography according to claim 21 including the step of nutating said detector array.

27. The method of computerized tomography according to claim 21 where said detector array comprises multiple single detector elements.

28. The method of computerized tomography according to claim 21 where said detector array comprises segmented detector elements.

29. The method of computerized tomography according to claim 21 where said X-ray source has a single focal spot.

30. The method of computerized tomography according to claim 21 where said X-ray source has multiple focal spots.

31. The method of computerized tomography of claim 21 where said step of reconstructing images corresponding to single planar sections enable a speed of the relative motion to be such that more than a planar section width is acquired by said detector elements per one revolution of said X-ray source.

32. The method of computerized tomography according to claim 21 where the relative motion speed is substantially constant.

33. The method of computerized tomography of claim 21 wherein said interpolating comprises interpolating between data acquired by a detector element of a given row at a given gantry angle and data acquired by another detector element at the given gantry angle in a following row and adjacent to the detector element of the given row.

34. The method of computerized tomography according to claim 33 where said interpolating step does non-linear interpolating between data as a function of said subject position.

35. The method of computerized tomography according to claim 33 where said interpolating step does linear interpolating between data as a function of said subject position.

36. The method of computerized tomography according to claim 33 where the step of reconstructing images from said scan includes interpolating between acquired multiple planar section data, said multiple planar section data being acquired simultaneously by detectors in adjacent rows.

37. A method of computerized tomography including the steps of:

supporting a scanned subject within an aperture of a gantry, mounting an X-ray source on said gantry, rotating said X-ray source at a substantially constant speed about said subject for at least two continuous revolutions, mounting an X-ray detector array on the side of said subject opposite to said X-ray source, said X-ray array comprised of a plurality of detector elements extending axially, simultaneously detecting X-rays that have traversed multiple planar sections in said subject during the rotating step, averaging the data detected at the same angle of rotation of said X-ray source during consecutive revolutions of said X-ray source, and reconstructing multiple images corresponding to planar sections measured simultaneously by said detector array, said images being reconstructed from said averaged data of multiple revolutions of said X-ray source.

\* \* \* \* \*